(12) United States Patent
Choy et al.

(10) Patent No.: US 7,288,318 B2
(45) Date of Patent: Oct. 30, 2007

(54) COSMETIC RAW MATERIALS HAVING IMPROVED PROPERTIES AND PROCESSES FOR PREPARING THE SAME

(75) Inventors: Jin Ho Choy, Seocho-gu (KR); Yang Su Han, Gwangmyeong-si (KR); Sung Ho Hwang, Gunpo-si (KR); Chi Won Lee, Dongjak-gu (KR); Jae Hun Yang, Jeju-si (KR); Sun Young Lee, Seodaemun-gu (KR)

(73) Assignee: Nanohybrid Co., Ltd., Seoul (KR)

( * ) Notice: Subject to any disclaimer, the term of this patent is extended or adjusted under 35 U.S.C. 154(b) by 0 days.

(21) Appl. No.: 10/484,706

(22) PCT Filed: Jul. 26, 2002

(86) PCT No.: PCT/KR02/01410

§ 371 (c)(1),
(2), (4) Date: Jan. 26, 2004

(87) PCT Pub. No.: WO03/011233

PCT Pub. Date: Feb. 13, 2003

(65) Prior Publication Data

US 2004/0171735 A1   Sep. 2, 2004

(30) Foreign Application Priority Data

Jul. 28, 2001 (KR) .............................. 2001-45697
Jul. 28, 2001 (KR) .............................. 2001-45703
Aug. 10, 2001 (KR) .............................. 2001-48177

(51) Int. Cl.
*B32B 5/16* (2006.01)

(52) U.S. Cl. ............ 428/402; 428/403; 428/404; 428/405; 428/407; 427/419.1

(58) Field of Classification Search ............ 428/402, 428/403, 404, 405, 407; 427/419.1
See application file for complete search history.

(56) References Cited

U.S. PATENT DOCUMENTS

| 4,727,167 A | * | 2/1988 | Burba et al. ............ 556/179 |
| 5,786,381 A | * | 7/1998 | Franklin et al. .......... 514/557 |
| 5,941,037 A | | 8/1999 | Hallock et al. |
| 5,977,212 A | | 11/1999 | Ebner et al. |

FOREIGN PATENT DOCUMENTS

WO    WO 96/16634 A1    6/1996

OTHER PUBLICATIONS

Meyn, M., et al., "Anion-Exchange Reactions of Layered Double Hydroxides", Inorganic Chemistry, American Chemical Society, Easton, US, vol. 29, 1990, pp. 5201-5207, XP008004649.

Meyn, M., et al. "Anion-Exchange Reactions of Hydroxy Double Salts", Inorganic Chemistry, American Chemical Society, Easton, US, vol. 32, No. 7, 1993, pp. 1209-1215, XP000568280.

* cited by examiner

*Primary Examiner*—Leszek Kiliman
(74) *Attorney, Agent, or Firm*—Rothwell, Figg, Ernst & Manbeck

(57) ABSTRACT

The present invention provides a hybrid material comprised of an active component for raw materials for cosmetics and a layered metal hydroxide, showing good stability, low toxicity, low irritation, good sustained release and good dispersibility. The present invention provides a method for preparing the hybrid material, using the coprecipitation method, the ion-exchange method or the adsorption method, depending on properties of the active component for raw materials for cosmetics. The method may further comprise a step of coating the surface of the hybrid material after preparation of the hybrid material. The present invention provides cosmectics comprising the above hybrid material.

38 Claims, 13 Drawing Sheets

COSMETIC RAW MATERIALS HAVING IMPROVED PROPERTIES AND PROCESSES FOR PREPARING THE SAME

CROSS REFERENCE TO RELATED APPLICATION

This application is a 35 USC § 371 National Phase Entry Application from PCT/KR02/01410, filed Jul. 26, 2002, and designating the U.S.

BACKGROUND OF THE INVENTION

1. Field of the Invention

The present invention relates to a hybrid material for use as raw materials for cosmetics and a method of preparation thereof. More specifically, it relates to a hybrid material for raw materials for cosmetics showing good safety, low toxicity, low irritation, good sustained release, good dispersibility, etc., and a method of preparation thereof.

2. Description of the Related Art

Human skin includes two layers, the epidermis and dermis. The epidermis consists of Keratinocytes which are keratin-forming cells, Melanocytes which are melanin-containing cells, and Langerhans which are cells related to immune function in the epidermis. The dermis has collagen which is an extra-cellular matrix (ECM) component, and fibroblast forming glycosaminoglycans (GAGs). These components must maintain their functions to keep human skin healthy and beautiful. However, as humans get older or their skin exposed to harmful environments such as ultraviolet lays, the concentration of reactive oxygen species (ROS) increases to accelerate oxidation, thereby resulting in phenomena such as pigmentary deposit, keratinization and wrinkles.

Thus, there have been various efforts to prevent or inhibit natural aging or temporary skin troubles occurring in skin. As part thereof, various natural and synthetic materials have been developed and used as raw materials for cosmetics for skin care. Such raw materials for cosmetics may be classified in terms of their functions into anti-oxidant, keratin remover, skin whitening agent, spot/freckle remover, skin calmative, skin moisturizing agent, skin activator, fire blight preventing agent, skin metabolism promoter, wrinkle preventing agent, etc.

Vitamins can be mentioned as one of most representative raw materials for cosmetics. Vitamins are essential materials for the body, having functions such as promoting body metabolism, anti-oxidation, protecting cell wall, enhancing immunity, increasing resistance to infection, etc. For human beings, biosynthesis of vitamins is impossible and thus intake of vitamins through food is essential. When vitamins are deficient, various diseases occur. In addition, vitamins play an important part in skin care and treatment such as preventing pigmentary deposit, promoting synthesis of collagen, blocking ultraviolet rays, preventing drying and keratinization of skin, preventing wrinkles and moisturizing skin. Exemplary vitamins include vitamin A such as retinol, vitamin C such as ascorbic acid, vitamin E such as tocopherol, and derivatives thereof.

In addition to vitamins, important raw materials for cosmetics include α-hydroxy acid (AHA) such as lactic acid, citric acid and salicylic acid, which functions to remove keratin layer of skin and thereby accelerate metabolism of skin; kojic acid (5-hydroxy-2-(hydroxymethyl)-4H-pyran-4-on) which functions to whiten skin by inhibiting melanin biosynthesis; indol-3-acetic acid ($C_{10}H_9NO_2$) which functions to prevent wrinkles by accelerating fibroblast multiplication; salicylic acid (2-hydroxy benzoic acid; $C_7H_6O_3$) which functions as an anti-oxidant to treat pimples; and other various known raw materials for cosmetics.

However, most of the aforementioned raw materials for cosmetics are limited in practical use because of problems in their inherent stability, skin irritation and toxicity, sustained release, dispersibility, etc., and thus have not exerted their functions and effects sufficiently. For example, vitamins are very unstable physicochemically and easily destroyed by heat, light, moisture, oxygen, alkali, etc., leading to deterioration of their functions and effects, or discoloration or malodor. Also, α-hydroxy acid such as lactic acid irritates skin. Kojic acid degenerates melanin pigments and melanin cells by penetrating into skin base layer, and thus if used in high concentration, induces various skin diseases such as dermatitis and skin cancer. It is also oxidized under light and high temperature to cause discoloration. Furthermore, indol-3-acetic acid is unstable under external environment, heat, light, moisture, oxygen, etc., especially light, to cause discoloration and malodor.

There have been many studies on formulation technologies to stabilize raw materials for cosmetics or reduce skin irritation or toxicity. In particular, such studies have been performed for vitamins, and based on them, studies on materials other than vitamins have been done.

Major prior stabilization methods for vitamins include oil-in-water (O/W) or water-in-oil (W/O) emulsion technology, multiple liquid crystal film technology, liposome technology, porous bead technology, water-soluble polymer technology and polysaccharide capsule technology.

Korean Patent No. 115706 discloses a method for preparing a vitamin nano-capsule by impregnating and sealing vitamin and various active components within an inner phase fine globule, and further stabilizing this using a double-layer lipid film. Furthermore, Korean Patent Laid-open Publication No. 2000-0048451 discloses a method for capsuling a lipophilic active component globule core with water insoluble synthetic or natural water-dispersible anionic polymers. Korean Patent Laid-open Publication No. 2000-0069893 discloses a method for stabilization by impregnating an active component in polysaccharide globule such as starch followed by coating the exterior with water-soluble polymers, or a method for stabilization by micro-emulsifying the active component and stabilizing the exterior using an anionic, non-ionic, cationic or amphionic surfactant.

Korean Patent No. 202401 discloses a method wherein an active component is impregnated in a polysaccharide and the exterior is capsuled with a neutral liquid crystal. Korean Patent No. 236484 discloses a method wherein a stable emulsion containing a water-soluble active component is formed and the exterior is further stabilized with a gelatin capsule. Korean Patent Laid-open Publication No. 1999-0070885 discloses a method wherein a mixture of vitamins such as water-soluble vitamins and fat-soluble vitamins is mixed with solid powder such as mica thereby absorbing into the powder and the surface thereof is coated with highly viscous liquid oil. Korean Patent No. 222000 discloses a stabilization method by applying simultaneously a liposome technology and a technology for forming liquid crystal. Korean Patent Laid-open Publication No. 2001-0002411 discloses a stabilization method by combination with natural materials such as coffee beans, tea leaves and cacao extracts.

Methods of using more stable derivative have been reported, but it has some problems. For example, magnesium ascorbyl phosphate can be easily converted into a form of biocompatible L-ascorbic acid compared to other derivatives, but it is difficult to be absorbed into skin. Ascorbyl palmitate is easily absorbed into skin, but difficult to be converted into a form of L-ascorbic acid.

Technologies for stabilizing vitamin A include oil-in-water or water-in-oil emulsion formulation technologies using an oil-soluble anti-oxidant such as butylated hydroxytoluene (BHT) or butylated hydroxy anisole (BHA), a water-soluble anti-oxidant such as ascorbic acid, or a chelating agent such as α-tocopherol. See Korean Patent Laid-open Publication Nos. 1990-021511 and 1999-0018726; U.S. Pat. Nos. 4,247,547; 4,826,828; 4,720,353; and 4,466,805; and EP 0 440 398 B1.

Japanese Patent Laid-open Publication No. Hei 2-83309 discloses a technology wherein a water-soluble L-ascorbic acid derivative is introduced into the inner phase of a water-in-oil emulsion to protect from oxidation or decomposition. Japanese Patent Laid-open Publication No. Sho 55-64511 discloses a technology wherein higher fatty acid esters are included within cyclodextrine. Japanese Patent Laid-open Publication No. Hei 3-5326 discloses a technology wherein L-ascorbic acid phosphoric acid esters or sulfuric acid esters are added to liposome to improve storage stability. Japanese Patent Laid-open Publication No. Hei 5-345714 discloses a technology wherein L-ascorbic acid esters are combined with certain water-soluble polymers to improve stability. All of these patent publications disclose using ester derivatives of L-ascorbic acid, which improves stability compared to L-ascorbic acid itself, but are known to be less effective in reducing melanin or inhibiting tyrosinase activities.

Korean Patent Laid-open Publication No. 2000-0026158 discloses a stabilization method using an oil-in-water emulsion which encapsulate retinol or derivatives based on a matrix of collagen and chitosan. However, retinol or derivatives are known to be thermodynamically very unstable. In particular, they are easily oxidized by oxygen in air, light and heat, resulting in loss of their effects and causing irritation to skin by decomposed retinol derivatives. BHA or BHT of the prior art may be added to stabilize retinol derivatives and reduce discoloration, but these components are also irritant to skin and recently avoided. There have been recent developments proposed on a number of methods for encapsuling with gelatin, alginic acid, etc., but these methods cause excess retinol to burst out at once and irritate skin.

The following methods are known. A method of microcapsuling tocopherol contained in the inner phase of retinyl palmitate, a fat-soluble active component with film material of crosslinked collagen and glucoseaminogrucane (Korean Patent Laid-open Publication No. 1999-0065437); a method of using double-capsuling consisting of first encapsuling an inner phase of retinol and secondly capsuling with gellane gum (Korean Patent Laid-open Publication No. 1998-21511); a method of capsuling in liposome (Korean Patent Laid-open Publication No. 1998-703668); a method of stabilizing retinyl palmitate in liquid crystal gel phase (Korean Patent Laid-open Publication No. 1996-033439). Additionally, a number of multi-emulsified forms, particularly W/O/W were also proposed to improve shortcomings of the prior single-emulsified forms such as W/O or O/W: see, U.S. Pat. No. 3,399,263, Great Britain Patent No. 1235667, Japanese Patent Laid-open Publication No. Sho 52-134029, Japanese Patent Laid-open Publication No. Sho 53-31578, Japanese Patent Laid-open Publication No. Sho 57-15829, Japanese Patent Laid-open Publication No. Sho 58-183611, Japanese Patent Laid-open Publication No. Sho 59-80326, Japanese Patent Laid-open Publication No. Sho 59-127646, Japanese Patent Laid-open Publication No. Sho 62-2561, Japanese Patent Laid-open Publication No. Sho 63-33311, Korean Patent Laid-open Publication No. 1995-0000131. There were also known methods wherein an active component is included in pores of porous microbeads in a similar manner to microcapsule (U.S. Pat. No. 5,145,675); and a method wherein the surface of porous microbeads containing an active component is treated with silicone or derivatives thereof (Korean Patent Laid-open Publication No. 2000-0067126).

As described above, the prior methods for stabilizing vitamins basically comprises combining a water-soluble or fat-soluble vitamin with oily or water phase polymers, surfactants and other organics thereby forming an inner phase, and if necessary, further encapsulating the exterior with polymers, surfactants, polysaccharides, oils, etc., although slightly different in specific matters.

In the case of α-hydroxy acid (AHA) such as lactic acid, citric acid and salicylic acid, there is no stability problem in using them as active components as raw materials for cosmetics, but if released in excess and applied to skin, they cause severe skin irritation such as torrid heat feeling and prickling. Thus, the amounts must be controlled when used as raw materials for cosmetics.

For kojic acid, Korean Patent Laid-open Publication No. 1998-044041 discloses a technology for preventing low molecular weight kojic acid from penetrating into skin, wherein a kojic acid is converted to a higher molecular weight by e.g. polymerizing the kojic acid using a kojic acid/amino acid complex. Furthermore, Korean Patent Laid-open Publication No. 2002-0025356 discloses a method for solving the problems of potency reduction and browning due to oxidation of kojic acid, using a kojic acid/amino acid complex and concentrated green tea extracts having the anti-oxidation effects. U.S. Pat. No. 4,847,074 discloses a technology for preventing browning and improving stability by including kojic acid within cyclodextrine. Furthermore, U.S. Pat. No. 4,369,174 discloses a method for improving stability against heat and light using derivatives obtained from the esterification reaction of kojic acid and aliphatic carboxylic acid.

In the case of indol-3-acetic acid, since its amount in a formulation is extremely small e.g. about 300 ppm, almost no separate report has been made on a stabilization method. Thus, prior stabilization methods for vitamins are mostly used for it. One prior art for indol-3-acetic acid is Korean Patent Application No. 2001-45629 which discloses a method for using it as a raw material for cosmetics by stabilizing it in the form of liposome.

The prior arts as described above have their own characteristics in degree of stabilization of each active component, release, delivery, biocompatibility, convenience, cost, and the like. However, there still remains a need for further improvements in safety, stability, sustained release, cost, and the like.

SUMMARY OF THE INVENTION

Therefore, the object of the present invention is to provide raw materials for cosmetics showing good safety, low toxicity, low irritation, good sustained release and good dispersibility.

Another object of the present invention is to provide a method for preparing the aforementioned raw materials for cosmetics, economically and effectively.

Another object of the present invention is to provide cosmetics comprising the aforementioned raw materials for cosmetics showing good safety, low toxicity, low irritation, good sustained release and good dispersibilty.

After making efforts to accomplish the above objects, it was discovered that hybrid materials of active components for raw materials for cosmetics and layered metal hydroxides show good safety, low toxicity, low irritation, good sustained release and good dispersibilty.

BRIEF DESCRIPTION OF THE DRAWINGS

The above and other features and advantages of the present invention will become more apparent by describing in detail exemplary embodiments thereof with reference to the attached drawings in which.

DETAILED DESCRIPTION OF THE INVENTION

Figure 1:
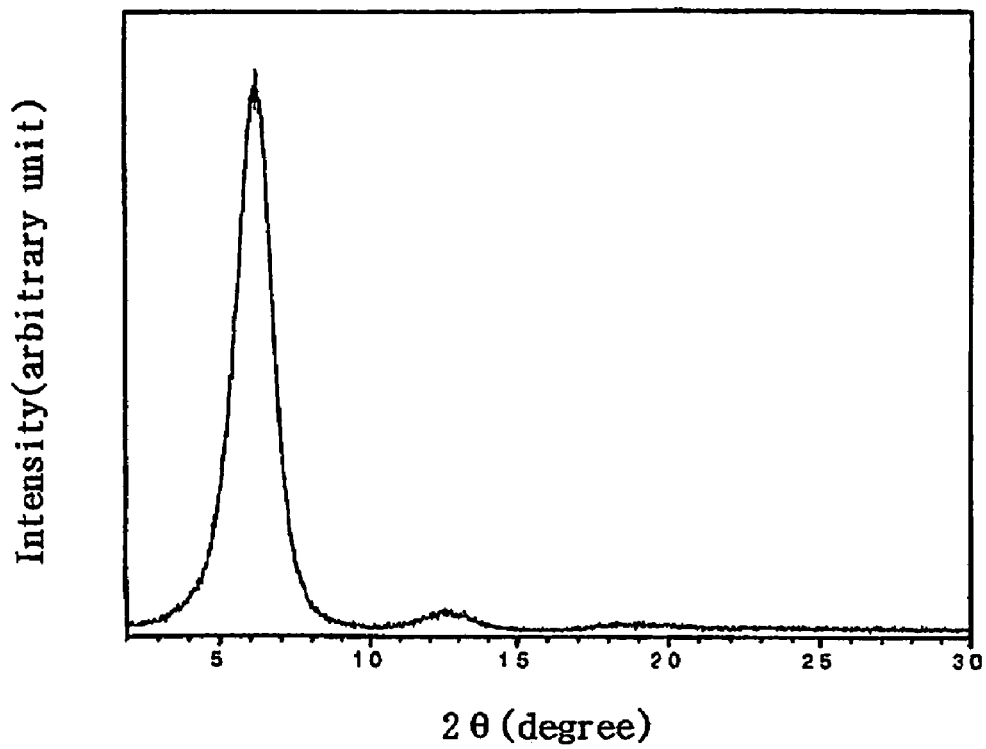
FIG. 1 is a powder X-ray diffraction pattern for a hybrid material of metal hydroxide and ascorbate (vitamin C) in the form of hydrozincyte prepared by the coprecipitation method.

"Layered metal hydroxides" as used in the present invention are weakly basic or neutral inorganic materials having good skin affinity without adverse effects such as skin irritation. Furthermore, the layered metal hydroxides have layered crystal structure and show peculiar reactivity between the layers. Also, they have anion exchange capacity, and thus can be effectively used for anionic components among active cosmetic components.

Layered metal hydroxides used in the present invention are preferably hydroxy double salts (HDS) or layered double hydroxides (LDHs). Among hydroxy double salts, those having a crystal structure of hydrozincyte ($Zn_5(OH)_6(CO_3)_2 \cdot nH_2O$) or zinc basic salts ($Zn_5(OH)_8Cl_2 \cdot nH_2O$) are more preferable. Layered double hydroxides are compounds such as hydrotalcyte having a formula of $[M(II)_{1-x}M(III)_x(OH)_2]^{x+} (A^{n-}{}_{x/n}) \cdot mH_2O$, where M(II) is a divalent metal cation such as Zn(II), Mg(II), Ca(II) and Fe(II); M(III) is a trivalent metal cation such as Al(III), Fe(III), Cr(III) and Co(III); and A is an anion. All these compounds have positive charges within hydroxide layers by different causes, and thus anions are present between the layers to compensate for the positive charges and may be replaced by other anionic species. Therefore, these compounds have capacity to stabilize negatively charged inorganic ions, organic ions or biomolecules between the layers.

Active components used in raw materials for cosmetics according to the present invention include natural or synthetic organic materials having the functions such as antioxidation, removing keratin, skin whitening, removing spots and freckles, skin sedation, skin moisturizing, skin activation, preventing fire blight, accelerating skin metabolism and preventing wrinkles. Examples include vitamins, α-hydroxy acids such as lactic acid, citric acid and salicylic acid, kojic acid (5-hydroxy-2-(hydroxymethyl)-4H-pyran-4-on), indol-3-acetic acid and salicylic acid (2-hydroxy benzoic acid).

Vitamins include, by way of example, vitamin A, vitamin C, vitamin E, etc., including pure vitamins and derivatives thereof. Examples of vitamin A include retinic acid ($C_{20}H_{28}O_2$), retinol ($C_{20}H_{30}O$), retinal ($C_{20}H_{28}O$), retinyl acetate ($C_{22}H_{32}O_2$) and retinyl palmitate ($C_{36}H_{60}O_2$). Examples of vitamin C include ascorbic acid ($C_6H_8O_6$) and ascorbate. Examples of vitamin E include α-tocopherol ($C_{29}H_{50}O_2$), tocopherol succinate ($C_{33}H_{54}O_5$) and tocopheryl acetate ($C_{31}H_{52}O_3$).

Furthermore, the present invention provides a method for preparing the aforementioned hybrid materials of active components for raw materials for cosmetics and layered metal hydroxides.

One embodiment of the method utilizes coprecipitation. This method comprises dissolving an active component for raw materials for cosmetics and starting materials for a layered metal hydroxide in an aqueous solvent or a mixed solvent, thereby causing precipitation. If necessary, a base may be added to induce precipitation.

The starting materials for the layered metal hydroxide are preferably those having high solubilities which are used in solvents and effectively cause precipitation in the form of layered metal hydroxides when a base is added. Therefore, although the layered metal hydroxide can be used directly, it is more preferable to use metal salts thereof such as metal carbonate, metal chlorides, metal nitrates and organic metal salts (e.g. acetate, oxalate and citrate). Examples include $ZnCl_2$, $Zn(NO_3)_3$, $Zn(CH_3COO)_2$, $MgCl_2$, $AlCl_3$, $CaCl_2$ or hydrates thereof.

The coprecipitation method is particularly suitable for active components having negative charges. Examples of such active components include retinic acid, L-ascorbic acid, tocopherol succinate, lactic acid, citric acid, salicylic acid, kojic acid, and indol-3-acetic acid.

A concentration of the metal ion in the coprecipitation method is e.g. 0.01 to 5 M. The amount of the active component is e.g. 0.1 to 10 equivalent moles relative to total moles of the metal components. Added bases include for example alkali metal hydroxide or an amine. The reaction solution is kept at pH 4 to 11, preferably pH 6 to 8, and the reaction temperature is 0 to 50° C., preferably 0 to 10° C. The reaction time is preferably 30 minutes or more. Furthermore, reaction is preferably performed with continuous purge by nitrogen or other inert gas and under shield.

Another embodiment of the method for preparing hybrid materials of active components for raw materials for cosmetics and layered metal hydroxides according to the present invention utilizes ion-exchange. This method comprises (1) reacting starting materials for a layered metal hydroxide in a basic solution to form a layered metal hydroxide salt, and (2) dispersing the layered metal hydroxide salt in an aqueous solvent or a mixed solvent, and dissolving an active component for raw materials for cosmetics, thereby causing ion-exchange reaction.

The ion-exchange method has a shortcoming in that the preparation process becomes more complex compared to the coprecipitation method. However, it is preferable as an alternative in a case where preparing the hybrid materials by the coprecipitation method is unsuitable.

Starting materials for layered metal hydroxides used in the ion-exchange method are the same as those described in the coprecipitation method. The amount of the active component added is e.g. 0.1 to 10 equivalent moles relative to the amount of metal hydroxide salts used. The reaction solution in the ion-exchange reaction is kept at e.g. about pH 5 to 11, preferably about pH 7 to 8. The reaction temperature is 0° C. to 50° C., preferably 0 to 10° C. The reaction time is preferably 30 minutes or more. Furthermore, the reaction is preferably performed with continuous purge by nitrogen or other inert gas and under shield.

Another embodiment of the method for preparing hybrid materials of active components for raw materials for cosmetics and layered metal hydroxides according to the present invention utilizes adsorption. This method comprises (1) reacting starting materials for a layered metal hydroxide and an organic acid or an anionic surfactant in an aqueous solvent or a mixed solvent to form organic-inorganic layered hybrid material, and (2) dispersing the said organic-inorganic layered hybrid material in an aqueous solvent or a mixed solvent, and adding an active component for raw materials for cosmetics, thereby adsorbing the active components onto the organic-inorganic layered hybrid material.

The adsorption method is particularly useful for neutral or highly hydrophobic active components. Such active components include retinol, retinal, retinyl acetate, retinyl palmitate, α-tocopherol and tocopheryl acetate.

In the adsorption method, suitable organic materials must be introduced onto the surface of the layered metal hydroxides when preparing the organic-inorganic layered hybrid materials. In order to accomplish this, the organic acid or anionic surfactant is introduced to make the surface of the layered metal hydroxides hydrophobic in the present invention. Examples of the organic acid include citric acid, stearic acid, succinic acid and tocopherol succinate. Examples of the anionic surfactant include dodecyl sulfate. Other preparation conditions are similar to those of the ion-exchange method.

"Hybrid materials" as the term is used herein do not refer to mere mixtures, but rather refer to such materials made based on chemical bonding forces between constituents. For example, in the case of cationic layered metal hydroxides and anionic raw materials for cosmetic active components, electrostatic interactions between the components having the counter ions act as the main chemical bonding force. Examples of a method based on such chemical bonding force include the coprecipitation method and the ion-exchange method. In the adsorption method, van der Waals force between the first introduced material, e.g. tocopherol succinate, and the later introduced material, e.g. retinol, is the main chemical bonding force. However, these are given by way of explanation and are not intended to limit the scope of the invention. Thus, in real conditions, electrostatic interactions and van der Waals force may coexist partly depending on constituents or preparation conditions.

Because the surface of the hybrid materials obtained as above is composed of inorganic materials, coagulation occurs during the preparation process through coprecipitation in a solution, or during the drying step, which causes deterioration of particle uniformity, mixibility, and dispersibility and dispersion stability.

One of the solutions to such problems includes a method of coating the surface of the obtained hybrid materials. Surface coating materials may be inorganic, organic or polymer materials which are harmless to the human body.

Inorganic coating materials include silica ($SiO_2$), titania ($TiO_2$) and alumina ($Al_2O_3$), but silica is most preferable in view of surface property modification performance, preparation process, cost of raw materials, etc. Raw materials of the inorganic coating materials include metal salts, e.g. $SiCl_4$, $TiCl_4$, $Si(OC_2H_5)_4$, $Si(OCH_3)_4$, $Ti(OC_3H_7)_4$ and $Al(OC_3H_7)_3$. Preferably, alkoxides such as $Si(OC_2H_5)_4$, $Si(OCH_3)_4$, $Ti(OC_3H_7)_4$ and $Al(OC_3H_7)_3$ is used. Surface coating using the inorganic coating materials are characterized by hydrolysis reaction between the hybrid materials and the coating raw materials. If necessary, a basic or acidic catalyst may be added.

In addition to the inorganic coating materials, various neutral surfactants having hydrophilic or lipophilic properties, and polymers such as polyvinyl alcohol, polyethylene glycol, cellulose and polymethyl methacrylate can be used alone or in combination. Alternatively, silane compounds and polymers can be used simultaneously for coating.

The present invention also provides cosmetics comprising the aforementioned hybrid materials of raw materials for cosmetics, active components and layered metal hydroxides. The cosmetics may comprise mediums and other additives conventionally used in cosmetics.

The hybrid materials according to the present invention show several properties distinguished from the materials prepared by prior stabilization methods. First, the hybrid materials according to the present invention have the particle size of tens of nm to several μm. If necessary, a drying step may be omitted to give products in the form of a suspension, colloid or slurry. Furthermore, products in the form of granules can be easily prepared to satisfy the conditions required for various formulation/addition processes. Second, since the hybrid material capsule consists of inorganic materials, stability is superior to prior capsules for stabilization. Furthermore, effects of blocking heat, light, moisture, oxygen, etc. are also excellent. In particular, degeneration of active components by heat or light is remarkably reduced. Third, the amount of active components per unit mass of the hybrid material capsule is very high compared to organic capsules. Fourth, the hybrid materials according to the present invention is biocompatible inorganics which show less adverse effects such as toxicity or irritation compared to prior materials for stabilization. Fifth, mixibility, dispersibility, dispersion stability, touch, convenience, etc. of the hybrid materials can be improved by surface coating. Sixth, cosmetics containing the hybrid materials as raw materials show additional functions such as blocking ultraviolet rays by the inorganic capsule materials and removing skin wastes by adsorption properties of the hybrid materials. Seventh, the preparation process is relatively simple and economical.

Furthermore, cosmetics containing the hybrid materials according to the present invention show less deterioration properties such as skin whitening, removal of keratin, preventing wrinkles, removing spots, skin moisturizing, blocking ultraviolet lays and removing skin wastes that are inherent to each active component due to the aforementioned properties of the hybrid materials.

The present invention will be described below in further detail by Examples. However, the Examples are only illustrative, and not intended to limit the scope of the invention.

EXAMPLES

Example 1

Figure 2:
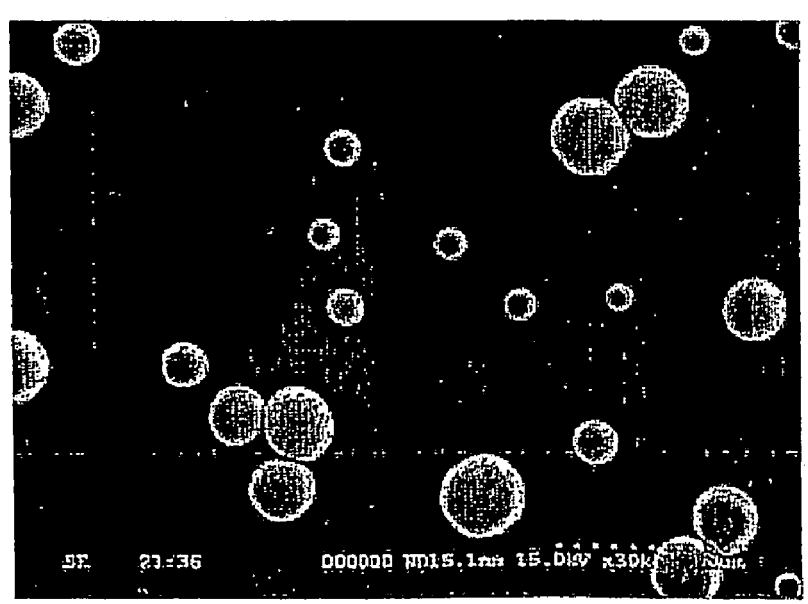
FIG. 2 is a scanning electron microgram for a hybrid material of metal hydroxide and ascorbate (vitamin C) in the form of hydrozincyte prepared by the coprecipitation method.

450 g of $Zn(CH_3COO)_2 \cdot 6H_2O$ was completely dissolved in 4 liters of distilled water and then 55 g of sodium ascorbate was added and again completely dissolved. 500 ml of 2 N NaOH solution was slowly added to the mixed solution to make pH of the solution 6.5, and precipitation was induced with stirring for 12 hours. The reaction temperature was kept below 10° C. Upon completion of the reaction, the precipitate and the filtrate were separated by centrifuge, and the precipitate was washed with distilled water 5 times or more to remove impurities. Then, the precipitate in slurry was dried using a freezing dryer to obtain the powder in fine particles. FIG. 1 is an X-ray diffraction pattern of the obtained hybrid material of zinc hydroxide and vitamin C. Analysis of the diffraction pattern shows that the hybrid material is a layered material in the form of hydrozincyte substituted by vitamin C. FIG. 2 is a field emission scanning electron microscopy (FE-SEM) micrograph of the hybrid material. The scan shows that the hybrid material consists of spherical fine particles of 100-200 nm mono-dispersion.

Example 2

The same conditions as those of Example 1 were used to produce a hybrid material of zinc hydroxide and vitamin C as obtained in Example 1, except using ascorbic acid instead of sodium ascorbate as the starting material.

Example 3

Figure 3:
FIG. 3 is a scanning electron microgram for a hybrid material of metal hydroxide and ascorbate (vitamin C) in the form of hydrozincyte prepared by the coprecipitation method using $Zn(NO_3)_2 \cdot 6H_2O$.

The same conditions as those of Example 1 was used to produce a hybrid material, except preparing a metal aqueous solution by dissolving 620 g of $Zn(NO_3)_2 \cdot 6H_2O$ instead of Zn-acetate in 4 liters of distilled water and using 175 g of ascorbic acid as the starting material of vitamin C. The hybrid material of zinc hydroxide and vitamin C prepared in the present Example showed an X-ray diffraction pattern similar to that of Example 1. This means that the product is also a layered compound having the crystal structure of hydrozincyte. FIG. 3 is a FE-SEM diagram of the vitamin hybrid material produced from $Zn(NO_3)_2 \cdot 6H_2O$ as the starting material, which shows the size and the structure of particles of the hybrid material. This shows that the average particle size of the hybrid material is about 50-100 nm.

Example 4

A hybrid material of L-ascorbic acid (vitamin C) and metal hydroxide in the form of hydrozincyte was synthesized using the ion-exchange method. 620 g of $Zn(NO_3)_2 \cdot 6H_2O$ was completely dissolved in 4 liters of distilled water. Then, 500 ml of 2 N NaOH solution was slowly added to the solution to make pH of the solution 4.5. Precipitation was induced with stirring for 12 hours. Reaction was performed at room temperature with continuous flow of nitrogen gas into the reaction solution. After 12 hours of reaction, the precipitate and the filtrate were separated using a centrifuge. The precipitate washed with distilled water 5 or more times to remove impurities. After washing, the precipitate in slurry was freeze-dried to obtain powder in fine particles. X-ray diffraction showed that the powder in fine particles obtained had the crystal structure of $Zn_5(OH)_8(NO_3)_2 \cdot nH_2O$ in the form of hydrozincyte. 0.1 g of thus obtained inorganic capsule material and 0.3 g of ascorbate were added to 100 ml of distilled water. Then, the ion-exchange reaction was performed with stirring to introduce ascorbate ions into the inorganic capsule material. The reaction solution was kept at about pH 7, and the reaction was performed for 24 hours with stirring. After completion of the ion-exchange reaction, a solid product was separated through a centrifuge, washed several times with distilled water, and freeze-dried to obtain a hybrid material of zinc hydroxide and vitamin C. The resulting hybrid material was found to have the same crystal structure as that of the hybrid material prepare in Example 3, using X-ray diffraction.

Example 5

Figure 4:
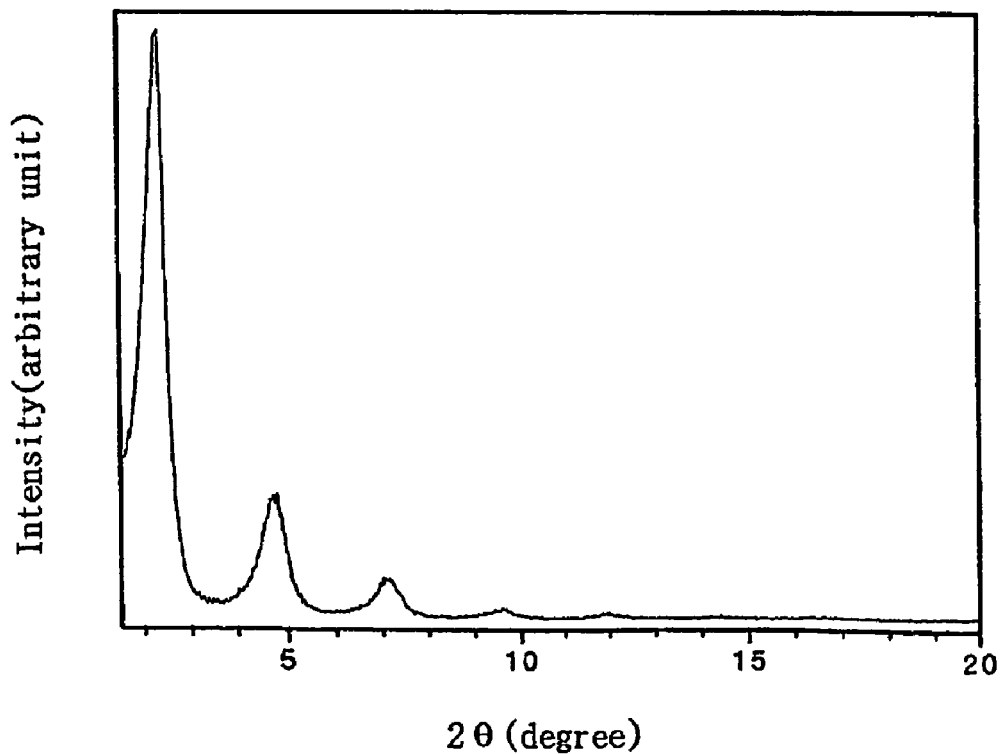
FIG. 4 is a powder X-ray diffraction pattern for a hybrid material of metal hydroxide and retinic acid in the form of hydrozincyte prepared by the coprecipitation method.
Figure 5:
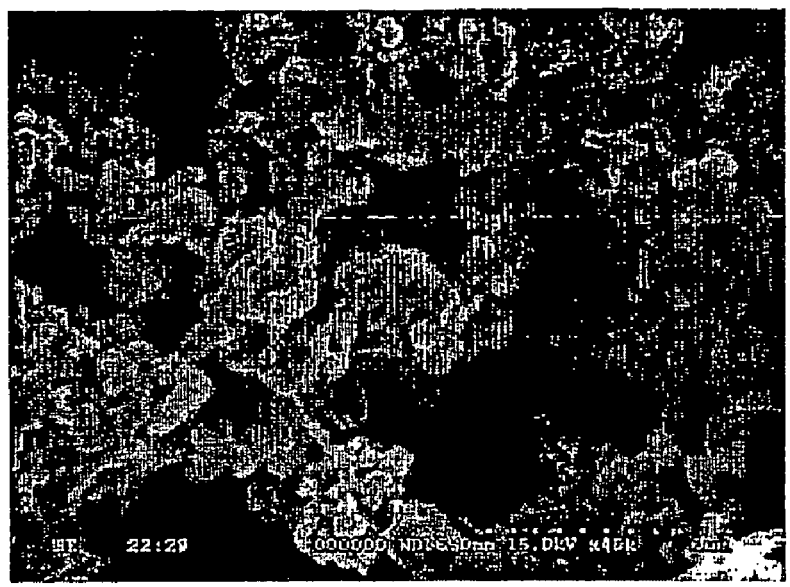
FIG. 5 is a scanning electron microgram for a hybrid material of metal hydroxide and retinic acid in the form of hydrozincyte prepared by the coprecipitation method.

6 g of $Zn(CH_3COO)_2 \cdot 6H_2O$ and 0.4 g of NaOH were completely dissolved in 0.3 liter of 25% ethanol solution. Then, 0.75 g of a retinic acid was added to the solution and completely dissolved. Precipitation was induced with stirring for 12 hours. Next, a hybrid material of zinc hydroxide and retinic acid (vitamin A) in fine powder with the other conditions kept the same as those of Example 1. FIG. 4 is an X-ray diffraction pattern of thus obtained hybrid material of zinc hydroxide and vitamin A. Analysis of the diffraction pattern shows that the hybrid material is a layered material substituted by vitamin A in the form of hydrozincyte. From element analysis and heat analysis of the metal ion and the organic, the molecular weight of the hybrid material was $Zn_5(OH)_8(vitamin A)_2 \cdot nH_2O$. FIG. 5 is a field emission scanning electron micrograph, which shows that the hybrid material is composed of mono-disperse spherical fine particles of about 50 nm.

Example 6

Figure 6:
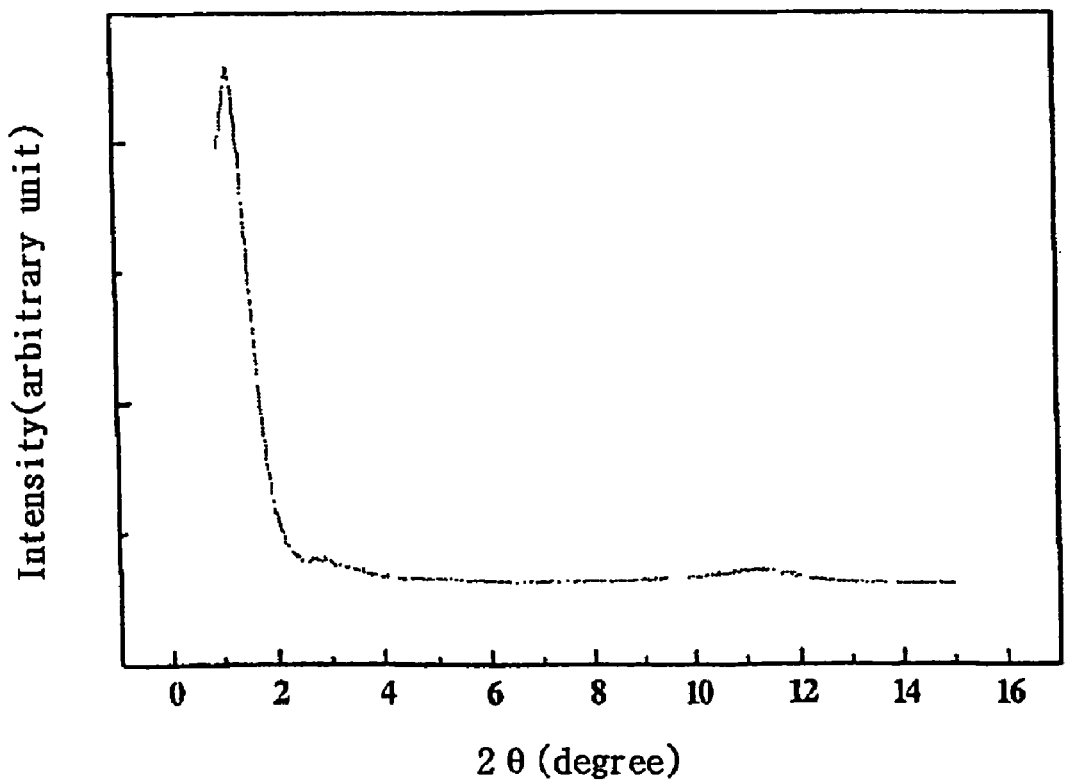
FIG. 6 is an X-ray diffraction pattern for a hybrid material of $Zn_3Al$-LDH-D-α-tocopherol succinate and retinol obtained by adsorbing vitamin A (retinol) into the layers of the hybrid material of $Zn_3Al$-LDH and D-α-tocopherol succinate prepared by the coprecipitation method.

A hybrid material of Zn/Al-LDH and D-α-tocopherol succinate-retinol (vitamin E derivative) was synthesized using the adsorption method. 4.09 g of $ZnCl_2$ and 1.33 g of $AlCl_3$ were dissolved in 400 mL of decarboxylated distilled water, and then 70 mL of an aqueous solution of D-α-tocopherol succinate (2.19 g) was added to the mixture. A coprecipitation reaction was performed by adding 1 N aqueous solution of NaOH to the mixed solution with stirring under the atmosphere of nitrogen to the final pH 7.5. The reaction was continued at room temperature for 12 hours. Then, the precipitate was separated from the reaction mixture by a centrifuge. The precipitate washed 5 times and freeze-dried to obtain a hybrid material of vitamin E and metal hydroxide. An X-ray diffraction pattern of thus obtained hybrid material showed that the distance between the layers was 47.0 Å, and that the hybrid material is vitamin E derivative arranged in the form of double-layers between the hydroxide layers. 1 g of thus obtained hybrid material was dispersed enough in 50 mL of ethanol. Then, 1 g of vitamin A (retinol) was dissolved and reacted under nitrogen atmosphere with stirring for 24 hours. After the reaction, solid/liquid was separated using a centrifuge, washed several times using ethanol, and dried to obtain a hybrid material of [vitamin E]-[vitamin A]-[inorganic]. FIG. 6 is an X-ray diffraction pattern of thus obtained hybrid material, which shows the distance between the layers is 72.1 Å, and the diffraction pattern moved to lower angle compared to that before adsorbing retinol. This is a phenomenon which occurs when vitamin A molecules are inserted between vitamin E derivatives that have already been inserted between the layers.

Example 7

Figure 7:
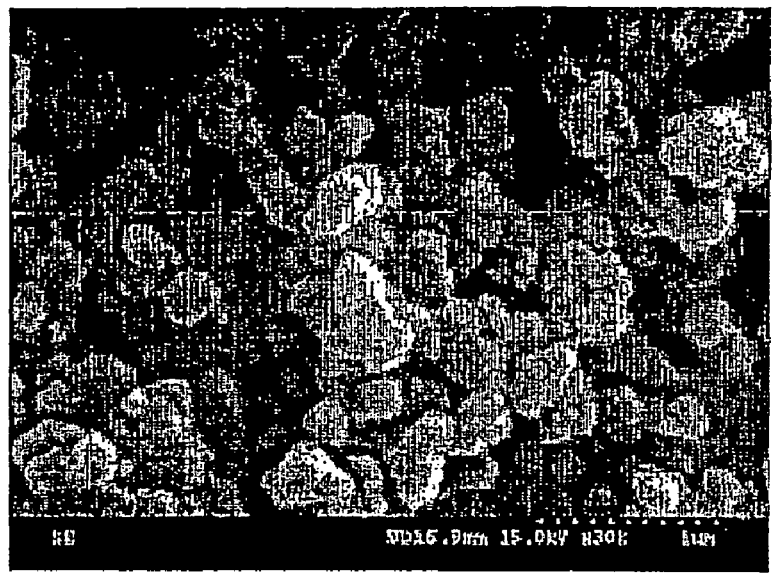
FIG. 7 is a field emission scanning electron microgram for $Zn_5(OH)_8(C_3H_5O_3)_2 \cdot nH_2O$ particles prepared by the coprecipitation method.

A hybrid material of lactic acid (α-hydroxy acid) and metal hydroxide in the form of hydrozincyte was synthesized using the coprecipitation method. 23 g of $Zn(NO_3)_2 \cdot 6H_2O$ was completely dissolved in 300 mL of distilled water, and then 9 g of lactic acid was added and completely dissolved. 100 ml of 0.5 N NaOH solution was slowly added to the mixed solution to make pH of the solution 6. Then, precipitation was induced with stirring under nitrogen atmosphere for 12 hours. After completion of the reaction, the precipitate and the filtrate were separated using a centrifuge, and the precipitate washed 5 times or more with distilled water to remove impurities. Then, the precipitate in slurry was dried under vacuum to obtain powder in fine particles. Analysis of an X-ray diffraction pattern shows that the hybrid material is a layered hydroxide containing anions of the lactic acid between the layers. FIG. 7 is a field emission scanning electron micrograph of the hybrid material, which shows that the hybrid material is composed of fine dispersed mono particles of 100 to 200 nm.

Example 8

Figure 8:
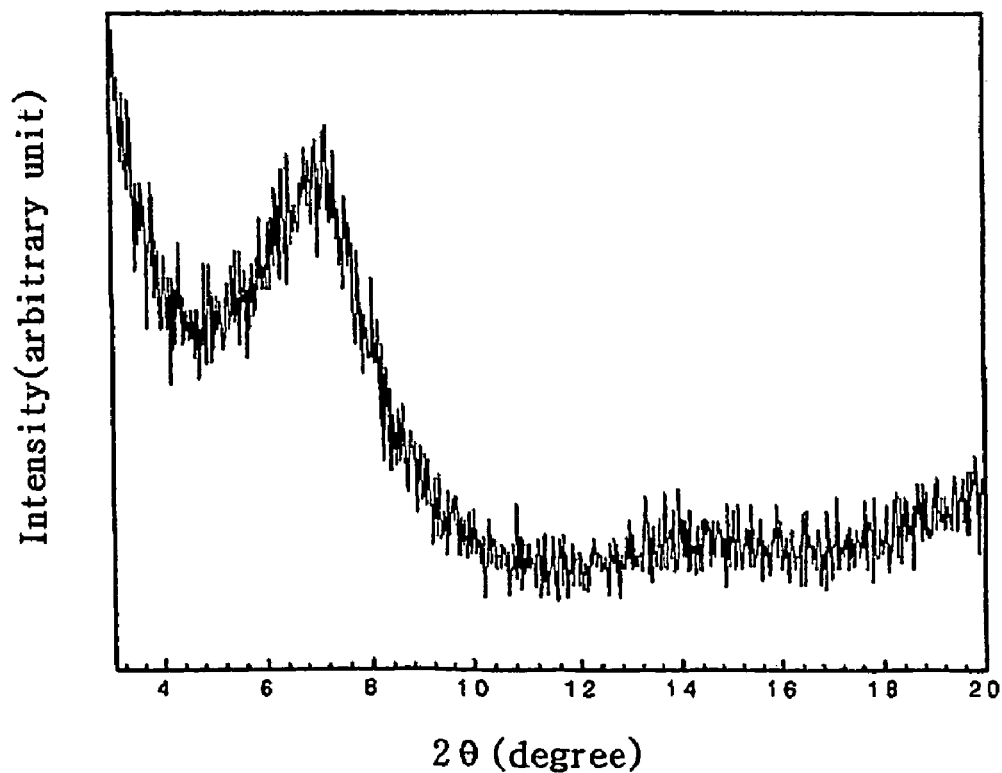
FIG. 8 is a powder X-ray diffraction pattern for $Zn_6Al_2(OH)_{16}(C_6H_5O_7)_{2/3} \cdot 4H_2O$ by the coprecipitation method.

A hybrid material of Zn/Al-LDH and citric acid was synthesized using the coprecipitation method. 465 g of $Zn(NO_3)_2 \cdot 6H_2O$ and 193 g of $Al(NO_3)_2 \cdot 9H_2O$ were completely dissolved in 3 L of distilled water, and then 74 g of citric acid was added and completely dissolved. 4 N NaOH solution was slowly added to the mixed solution to make pH of the solution 8. Then, precipitation was induced with stirring for 12 hours. After completion of the reaction, the precipitate was separated, washed and dried in the same manner as in Example 7 to obtain powder of the hybrid material in fine particles. FIG. 8 is an X-ray diffraction pattern of the obtained hybrid material of Zn/Al-LDH and citric acid. Analysis of the pattern shows that the hybrid material is a layered double hydroxide in the form of hydrotalcyte containing anions of the citric acid between the layers.

Example 9

Figure 9:
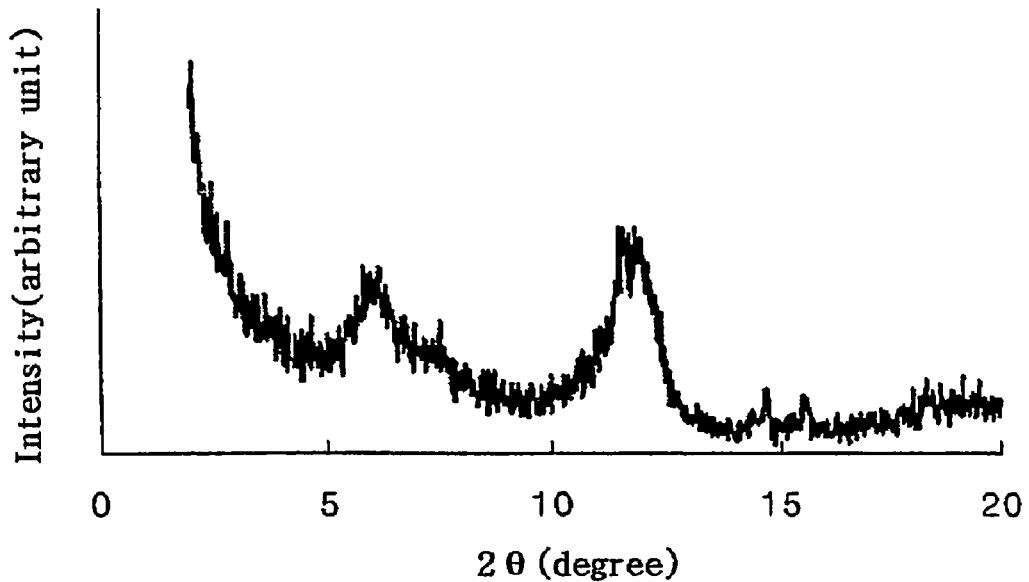
FIG. 9 is a powder X-ray diffraction pattern for a hybrid material of metal hydroxide and kojic acid in the form of hydrozincyte prepared by the coprecipitation method.

A hybrid material of kojic acid and hydrozincyte-form metal hydroxide was synthesized using the coprecipitation method. 10.34 g of kojic acid ($C_6H_6O_4$; molecular weight=142.11 g/mol) was completely dissolved in a mixed solution of 100 mL of decarboxylated water and 100 mL of ethanol, and then 0.6 N NaOH aqueous solution was added to make pH of the solution 9~10. 18 g of $Zn(NO_3)_2 \cdot 6H_2O$ was dissolved in 100 mL of decarboxylated water in another vessel, and then this aqueous metal solution was added to the solution containing the kojic acid. At the same time, pH of the reaction solution was adjusted to about 9 to 10 using 0.6 N NaOH aqueous solution. After completion of the titration, the solution was reacted at room temperature for 20 hours. After completion of the reaction, the precipitate was separated from the filtrate using a centrifuge, and washed using 5 times or more using distilled water to remove impurities. Then, the precipitate in slurry was dried under vacuum to obtain powder in fine particles. FIG. 9 is an X-ray diffraction pattern of thus obtained hybrid material, which shows that a distance between the layers is 14.6 Å. This means that the hybrid material is a layered hydroxide containing anions of the kojic acid between the layers.

Example 10

Figure 10:
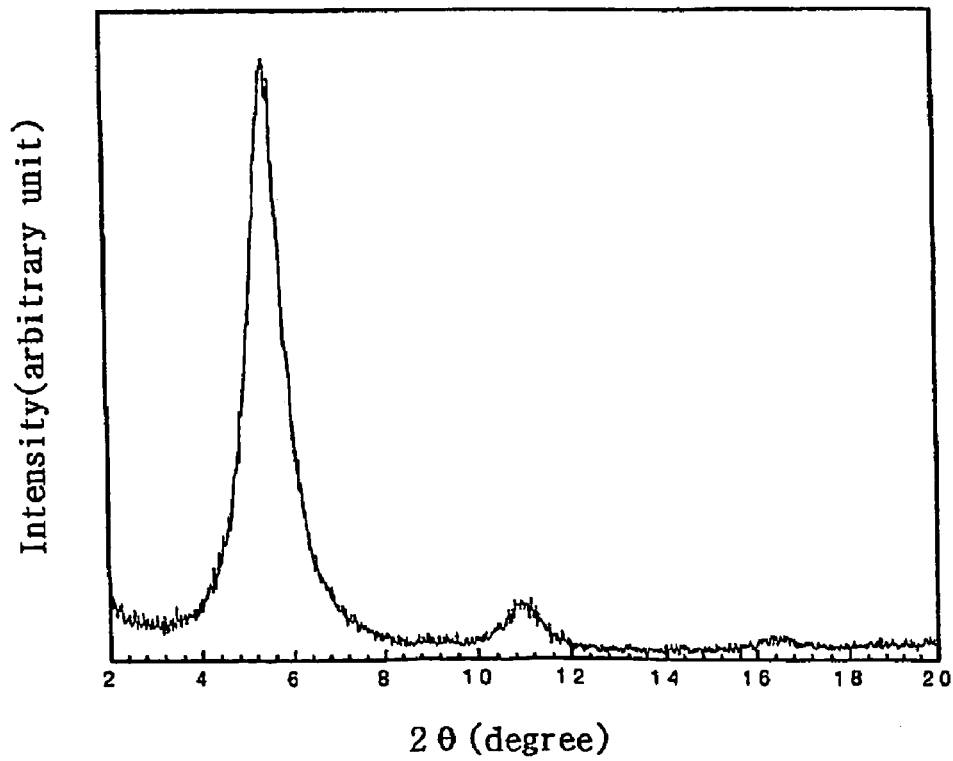
FIG. 10 is a powder X-ray diffraction pattern for $Zn_5(OH)_8(C_7H_5O_3)_2 \cdot nH_2O$ particles prepared by the coprecipitation method.

The same conditions as those of Example 7 were used to produce a hybrid material, $Zn_5(OH)_8(salicylic\ acid)_2 \cdot 4H_2O$, except that 2.3 g of salicylic acid ($C_7H_6O_3$) was used, and the solution was kept at pH 6. An X-ray diffraction pattern of the hybrid material is shown in FIG. 10.

Example 11

Figure 11:
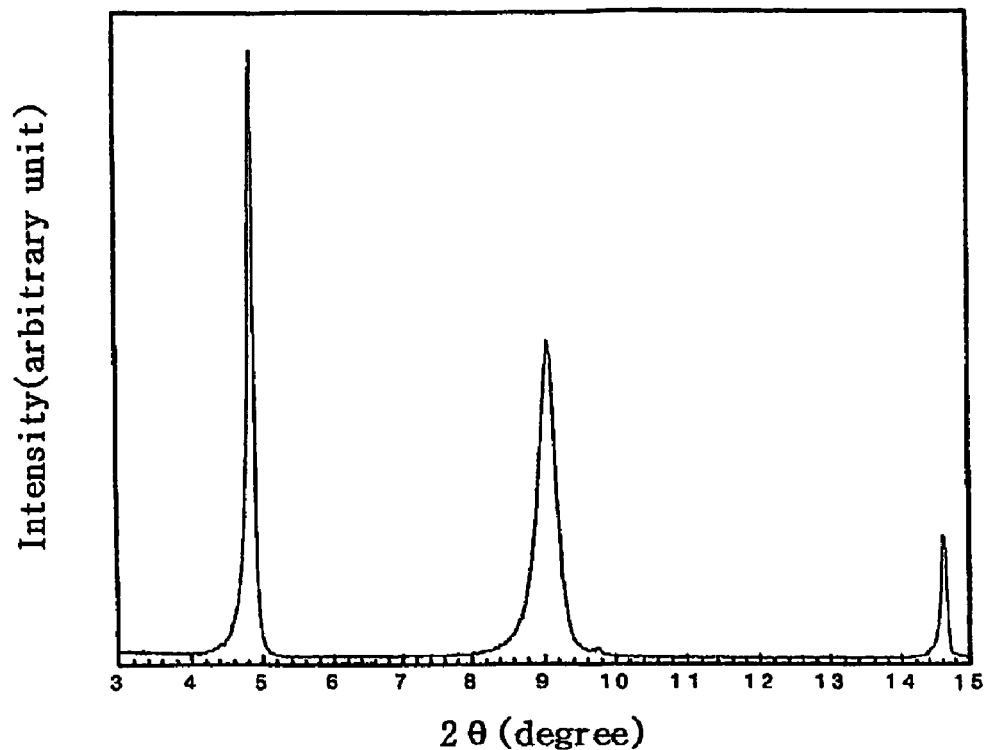
FIG. 11 is a powder X-ray diffraction pattern for $Zn_5(OH)_8(C_{10}H_8NO_2)_2 \cdot nH_2O$ particles prepared by the coprecipitation method.
Figure 12:
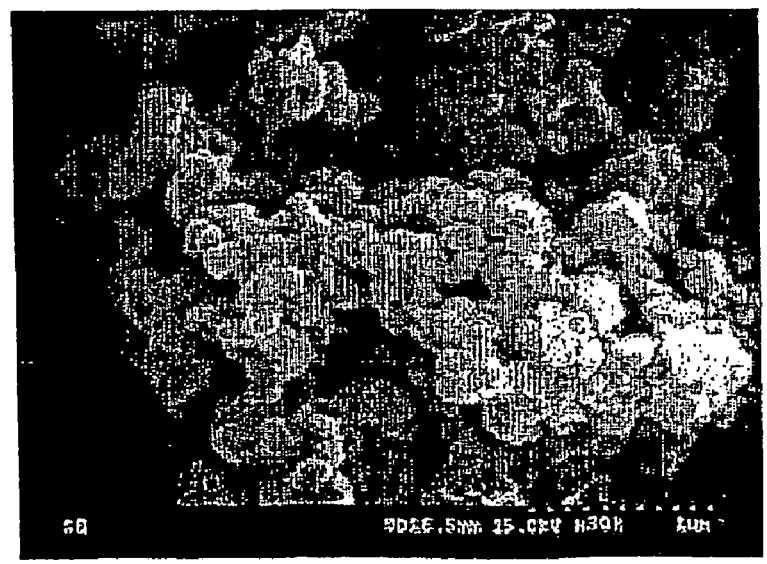
FIG. 12 is a field emission scanning electron microgram for $Zn_5(OH)_8(C_{10}H_8NO_2)_2 \cdot nH_2O$ particles prepared by the coprecipitation method.

37 g of $Zn(NO_3)_2 \cdot 6H_2O$ was completely dissolved in 120 ml of decarboxylated distilled water, and then 10 g of indol-3-acetic acid was completely dissolved in 15 ml of decarboxylated distilled water and 120 ml of ethanol. Then, 50 ml of 1.6 N NaOH solution was slowly added to the mixed solution to make pH of the solution 6.7, and precipitation was induced by stirring for 6 hours. The reaction temperature was kept below 10° C. The precipitate was sufficiently washed and dried to obtain powder in fine particles. An X-ray diffraction pattern of thus obtained hybrid material is shown in FIG. 11, and a scanning electron micrograph is shown in FIG. 12. The X-ray pattern shows that a distance ($d_{001}$) between the layers is 18.2 Å, and this means that molecules of indol-3-acetic acid are stabilized between the layers of the hydroxide, and that the produced hybrid material is fine particles of 100 to 200 nm.

Example 12

Figure 13:
FIG. 13 is a scanning electron microgram for particles of a hybrid material of metal hydroxide and vitamin C, surface-coated with silica using tetraethoxysilicate (TEOS), the hybrid material being in the form of hydrozincyte in slurry phase prepared by the coprecipitation method.

100 g of the precipitate prepared in Example 3 in slurry was added to a mixed solution of 100 g of tetraethoxysilicate (TEOS; $Si(OC_2H_5)_4$) dispersed in 400 ml of ethanol, and stirred for 1 hour. Then, 100 ml of distilled water was added to the reaction solution to perform a coating reaction. The coating reaction was carried out at room temperature for 24 hours. After completion of the reaction, the solid product was separated using c centrifuge, and then washed two times using ethanol. Thus obtained solid material was dried in a vacuum drier for 24 hours to give powder in fine particles. FIG. 13 is a field emission scanning electron micrograph, which shows that silica particles of 20 to 30 nm is coated onto the surface of the hybrid material, and many pores have been formed between the particles.

Example 13

Figure 14:
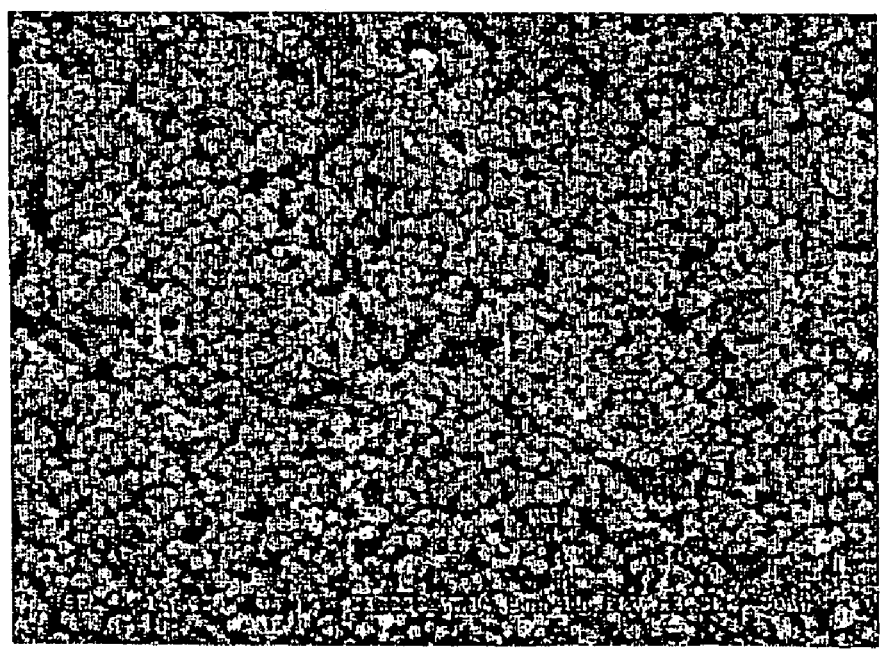
FIG. 14 is a scanning electron microgram for particles of a hybrid material of metal hydroxide and vitamin C, surface-coated with silica by adding tetraethoxysilicate (TEOS) to a suspension of the hybrid material without additional separation or washing step, the hybrid material being in the form of hydrozincyte prepared by the coprecipitation method.

A hybrid material of hydrozincyte-type metal hydroxide and vitamin C was synthesized, and without separate separation or washing step, tetraethoxysilicate (TEOS) was directly added to coat the surface of the hybrid material with silica ($SiO_2$). 42.70 g of ascorbic acid was completely dissolved in 60 mL of decarboxylated water, and then an aqueous solution of 185.92 g of $Zn(NO_3)_2 \cdot 6H_2O$ dissolved in 300 mL of decarboxylated water was added in drops. At the same time, 240 mL of 1.6 N NaOH aqueous solution was titrated, and reacted for 5 hours to obtain the hybrid material of vitamin C and hydrozincyte in coprecipitate. After completion of the reaction, without washing step, a mixed solution of 394.68 g of TEOS and 2.4 L of ethanol was slowly added in drops to the suspension of the above hybrid material. Then, the coating reaction was carried out for a further 12 hours. After completion of the reaction, the reaction mixture was centrifuged, washed with ethanol 4 times, and dried to obtain the hybrid material coated with silica. FIG. 14 is a scanning electron micrograph of thus obtained particles, which shows that particles having a size of about 0.5 μm have been formed.

Example 14

Figure 15:
FIG. 15 is a scanning electron microgram for particles of a hybrid material of metal hydroxide and vitamin C, surface-coated with silica using tetraethoxysilicate (TEOS), the hybrid material being in powder form prepared by the coprecipitation method.

The hybrid material obtained in Example 3 in slurry was freeze-dried to produce powder. The powder was surface-coated with silica in the same way as in Example 12. In doing this, 5 g of the dried hybrid material was added to a mixed solution of 20 g of TEOS dispersed in 80 ml of ethanol, and stirred for 1 hour. Then, 20 ml of distilled water was added to the reaction solution, and the coating reaction was carried out at room temperature for 24 hours. After completion of the coating reaction, the product washed and dried in the same way as in Example 12 to obtain a product in particles. FIG. 15 is an electron microgram of thus coated material. This shows that, like Example 14, silica particles of tens of nm have been coated onto the surface of the hybrid material and many pores have been formed between the particles.

Example 15

Figure 16:
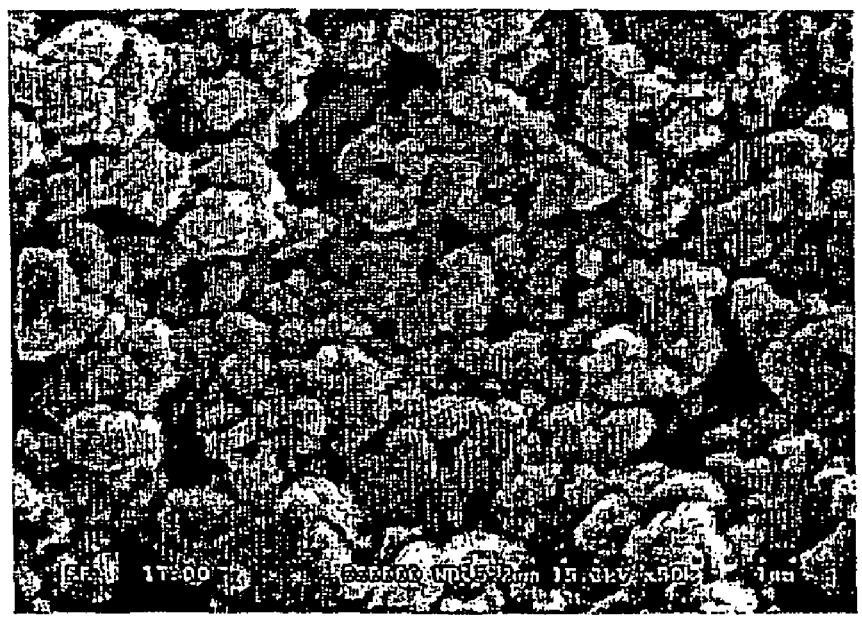
FIG. 16 is a scanning electron microgram for particles of a hybrid material of metal hydroxide and vitamin C, surface-coated with silica using tetramethoxysilicate (TMOS), the hybrid material being in the form of hydrozincyte in slurry phase prepared by the coprecipitation method.

100 g of the slurry-phase precipitate obtained in Example 3 was added to a mixed solution of 100 g of tetramethoxy-silicate (TMOS; $Si(OCH_3)_4$) dispersed in 400 ml of methanol. After stirring for 1 hour, 100 ml of distilled water was added and the coating reaction was carried out at room temperature for 24 hours. After completion of the reaction, a solid product was separated using a centrifuge, and washed two times using ethanol. Then, the obtained solid material was dried in a vacuum drier for 24 hours to obtain powder in fine particles. FIG. 16 is a field emission scanning electron microgram of thus coated hybrid material, which shows that silica particles of 20 to 30 nm have been coated onto the surface of the hybrid material and many pores have been formed between the particles when coated using TMOS as well.

Example 16

Figure 17:
FIG. 17 is a scanning electron microgram for particles of a hybrid material of metal hydroxide and vitamin C, surface-coated with silica using tetraethoxysilicate (TEOS) and an acid catalyst, the hybrid material being in the form of hydrozincyte in slurry phase prepared by the coprecipitation method.

100 g of the slurry-phase precipitate obtained in Example 3 was added to a mixed solution of 100 g of tetraethoxy-silicate (TEOS; $Si(OC_2H_5)_4$) dispersed in 400 ml of ethanol, and then the coating reaction was carried out with stirring. At this time, a small amount of 1 N HCl solution was added in drops to adjust pH of the reaction solution to 5, thereby inducing the coating reaction under a weakly acidic condition. The coating reaction was carried out at room temperature for 24 hours. After completion of the reaction, a solid product was separated using a centrifuge, and washed two times using ethanol. Then, the obtained solid material was dried in a vacuum drier for 24 hours to obtain powder in fine particles. FIG. 17 is a field emission scanning electron micrograph of thus coated hybrid material, which shows that uniformity of the surface coating has been improved using an acid catalyst during the coating reaction.

Example 17

Figure 18:
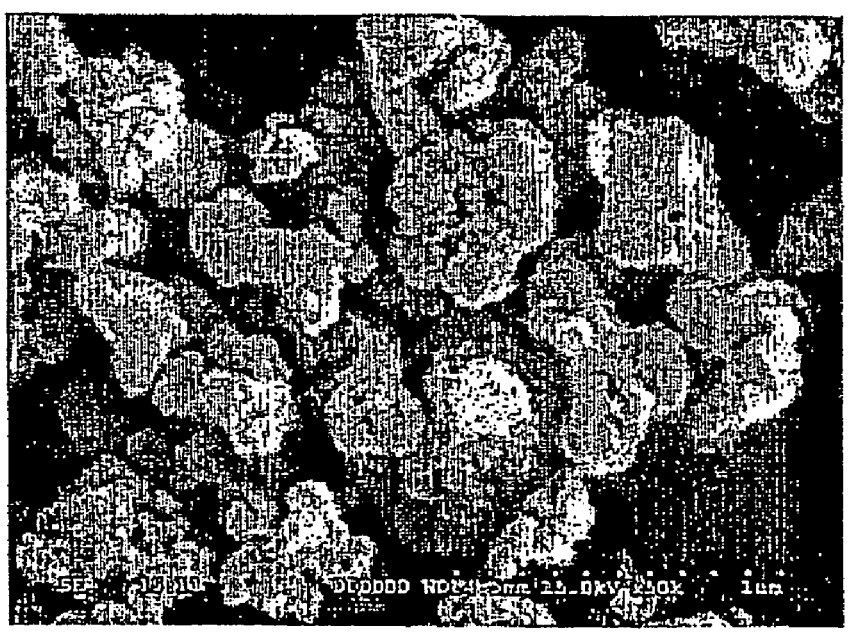
FIG. 18 is a scanning electron microgram for particles of a hybrid material of metal hydroxide and vitamin C, surface-coated with silica using tetraethoxysilicate (TEOS), the hybrid material being in the form of ZnAl-LDH in slurry phase prepared by the ion-exchange method.

A hybrid material of L-ascorbic acid (vitamin C) and Zn/Al-LDH was synthesized using the ion-exchange method. Using the metal salts $Zn(NO_3)_2.6H_2O$ and $Al(NO_3)_3.9H_2O$ as starting materials, an aqueous solution containing the metal ions Zn(II) and Al(III) in suitable mole ratio (Zn/Al=2) was prepared. Then, 0.2 N NaOH solution was added in drops to the solution to obtain a layered double hydroxide with nitric acid anions ($NO_3^-$) inserted between the layers. The precipitate washed enough and dried to obtain a LDH precursor in the form of fine powder. This was mixed with an aqueous solution containing vitamin C to allow ion-exchange with nitric acid anions between the layers, thereby obtaining a hybrid material of vitamin C and the layered metal hydroxide. In doing this, a mole ratio of vitamin C to the inorganics, [vitamin C]/[Al], was 1.5, and the reaction was carried out with stirring at room temperature for 24 hours. An X-ray diffraction analysis of thus obtained hybrid material of vitamin C and Zn/Al-LDH shows that the distance between the layers is 10.5 Å, and that vitamin C molecules have been stabilized as a single layer parallel with the layer of the metal hydroxide. The hybrid material thus obtained by the ion-exchange was surface-coated with silica using TEOS as a precursor. The coating reaction was carried out by adding the hybrid material precipitate in slurry to a mixed solution of 100 g of TEOS dispersed in 400 ml of ethanol and stirring for 1 hour, followed by adding 100 ml of distilled water to the reaction solution. The subsequent procedures were the same as those in Example 12. FIG. 18 is a scanning electron micrograph, which shows that the hybrid material in the form of LDH as well has been surface-coated with silica particles.

Example 18

Figure 19:
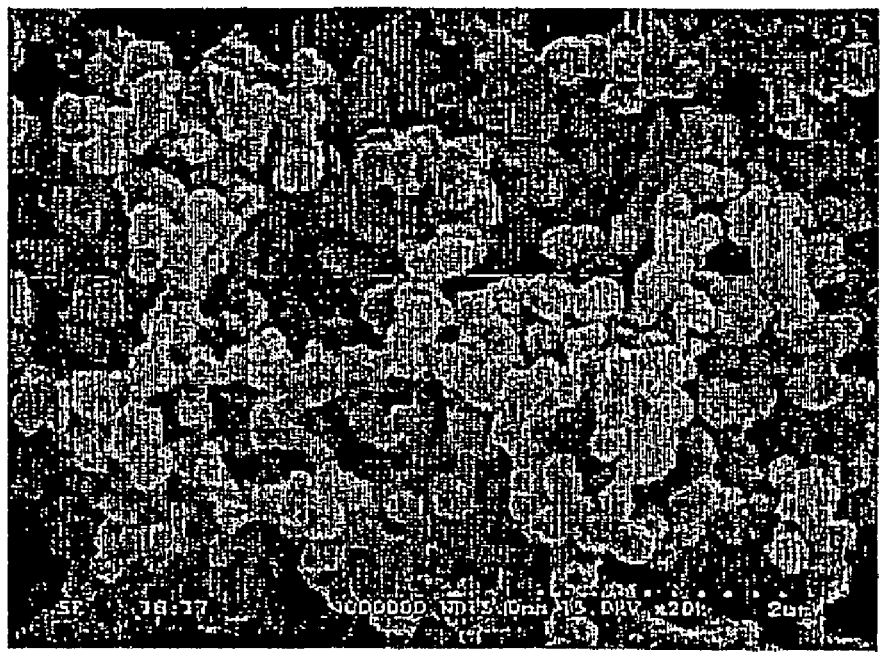
FIG. 19 is a scanning electron microgram for particles of a hybrid material of metal hydroxide and vitamin C, secondary-coated with silane and polymethylmethacrylate (PMMA), the hybrid material being in the form of hydrozincyte prepared by the coprecipitation method.

The slurry-phase precipitate obtained in Example 3 washed two times using ethanol, and solid/liquid separated using a centrifuge to obtain a gel. 40 g of thus obtained gel was dispersed in 80 mL of ethanol, and stirred under nitrogen atmosphere. Also, 10.7 g of TMOS and 2.9 g of γ-methacryloxypropyl-trimethoxysilane were added to 93 mL of ethanol. To this solution, 1.5 mL of 0.1 N HCl aqueous solution was added and hydrolyzed at ambient temperature for 30 minutes. Then, this solution was added to the above gel dispersion and stirred at ambient temperature for 30 minutes for reaction. 2.25 g of 2,2'-azobiisobutyronitrile was added to this solution and after 5 minutes 29.2 mL of methylmethacrylate was added. After reaction at 60° C. with stirring for 4 hours, solid was separated using a centrifuge, washed two times with ethanol, and dried under vacuum to obtain a hybrid material coated with silica-PMMA. A scanning electron micrograph of thus obtained hybrid material is shown in FIG. 19. This shows that very uniform and mono-disperse hybrid material has been obtained.

Example 19

Figure 20:
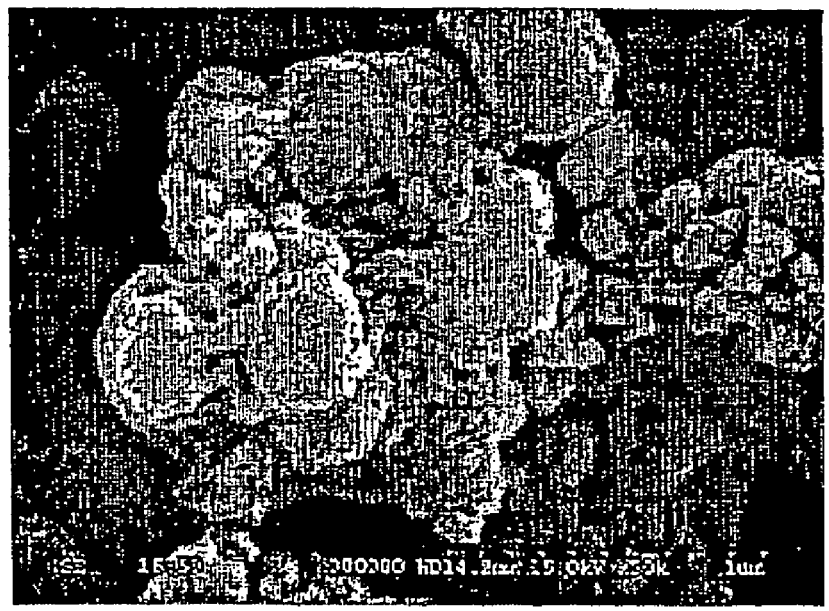
FIG. 20 is a scanning electron microgram for particles of a hybrid material of metal hydroxide and vitamin C, secondary-coated with polymethylmethacrylate (PMMA) by solution polymerization method, the hybrid material being in the form of hydrozincyte coated with silica.

5 g of the particulate material obtained in Example 12 was introduced into a 250 mL conical flask, and sealed with a silicon stopper under nitrogen-filled condition. Then, 15 g of absolute methanol and 2.5 g of methyl methacrylate were added using a syringe, and stirred. Also, 0.1 g of 2,2'-azobiisobutyronitrile (AlBN) was dissolved in 3.75 g of absolute methanol, and this solution was added to the above reactor by a syringe. To absorb the internal pressure, a rubber balloon was put up in the reactor. The solution was reacted with stirring at 60° C. for 24 hours. After completion of the reaction, solid was separated using a centrifuge, washed two times with ethanol, and dried under vacuum to obtain PMMA-coated powder. A scanning electron micrograph of the PMMA-coated hybrid material is shown in FIG. 20.

Example 20

Figure 21:
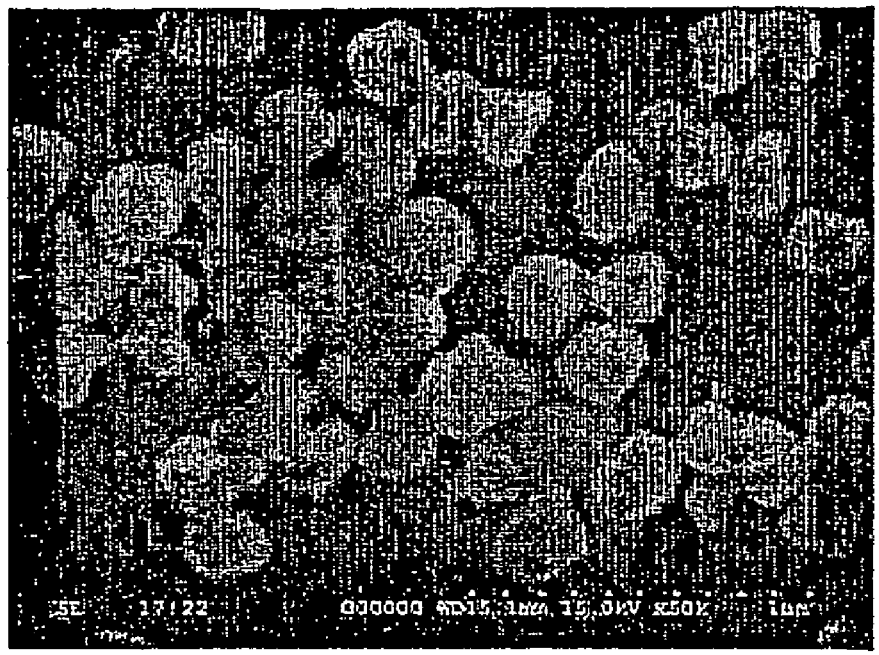
FIG. 21 is a scanning electron microgram for particles of a hybrid material of metal hydroxide and vitamin C, secondary-coated with ethyl cellulose in a solution, the hybrid material being in the form of hydrozincyte coated with silica.

The particulate material obtained in Example 12 was surface-coated using cellulose. 10 g of the particulate material and 30 g of Tween 20, a neutral surfactant, was added into 200 mL of distilled water and dispersed well. 5 g of ethyl cellulose dissolved in methylene chloride was added to the solution containing the silica-coated vitamin hybrid material and emulsified. This emulsion was stirred using a homogenizer until methyle chloride is evaporized up, and centrifuged. The obtained gel washed three times with distilled water, and then dried under vacuum to obtain powder coated with ethyl cellulose. A scanning electron microscopy of thus obtained hybrid material is shown in FIG. 21. This shows that coated particles having a good mono-dispersity have been obtained by the surface treatment using ethyl cellulose.

Example 21

Figure 22:
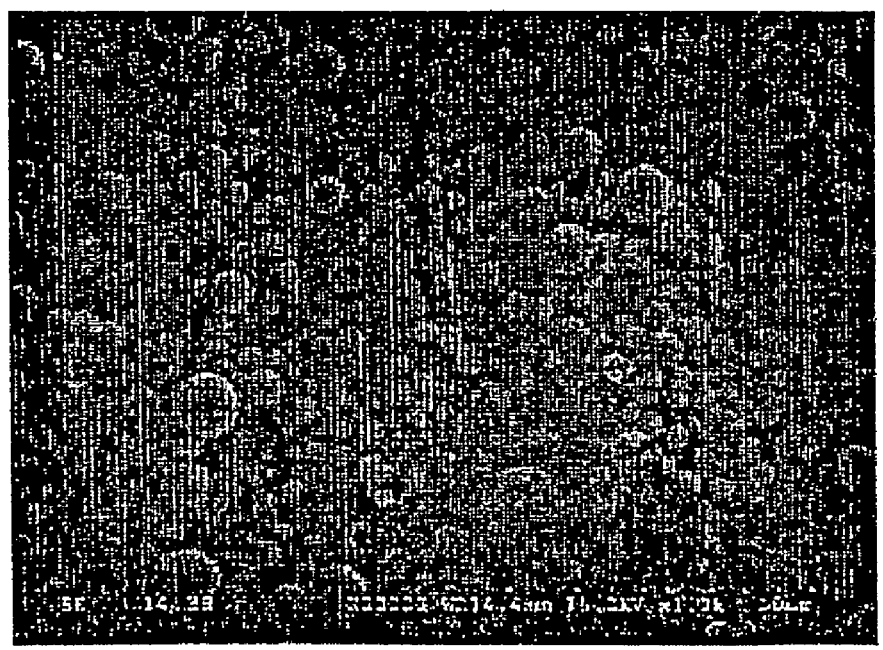
FIG. 22 is a scanning electron microgram for particles of a hybrid material of metal hydroxide and vitamin C, secondary-coated with polyvinyl alcohol (PVA) and polymethylmethacrylate (PMMA) in a solution, the hybrid material being in the form of hydrozincyte coated with silica.

The particulate material obtained in Example 12 was surface-coated using polymethylmethacrylate (PMMA). 2.5 g of the particulate material was added into 200 mL of aqueous solution containing 1.0 w/v % of polyvinyl alcohol, and dispersed well. Then, 5 g of polymethylmethacrylate dissolved in 300 mL of methylene chloride was added to the dispersion of the vitamin hybrid material, and emulsified. This emulsion was stirred using a homogenizer until methyle chloride is vaporized, then, centrifuged. The obtained gel washed three times with distilled water, and then dried under vacuum to obtain powder coated with polymethylmethacrylate. A scanning electron microscopy of thus obtained hybrid material is shown in FIG. 22. This shows that uniform spherical coating particles have been obtained.

Example 22

Figure 23:
FIG. 23 is a scanning electron microgram for a hybrid material of $Zn_5(OH)_8(C_{10}H_8NO_2)_2 \cdot nH_2O$ obtained in Example 11, surface-coated with silica using tetraethoxysilicate (TEOS)

$Zn_5(OH)_8(C_{10}H_8NO_2)_2.nH_2O$ obtained in Example 11 was surface-coated using silica. The coating reaction was carried out for 12 hours by stirring 1 g of the above hybrid material in 10 ml of an aqueous solution for 1 hour to dispersion, and then adding in drops 1 g of TEOS (Si$(OC_2H_5)_4$) dissolved in 10 ml of ethanol. FIG. 23 is a scanning electron micrograph of the hybrid material coated with silica, which shows that silica of 20 to 30 nm has been uniformly coated onto the surface of the hybrid material.

Example 23

Figure 24:
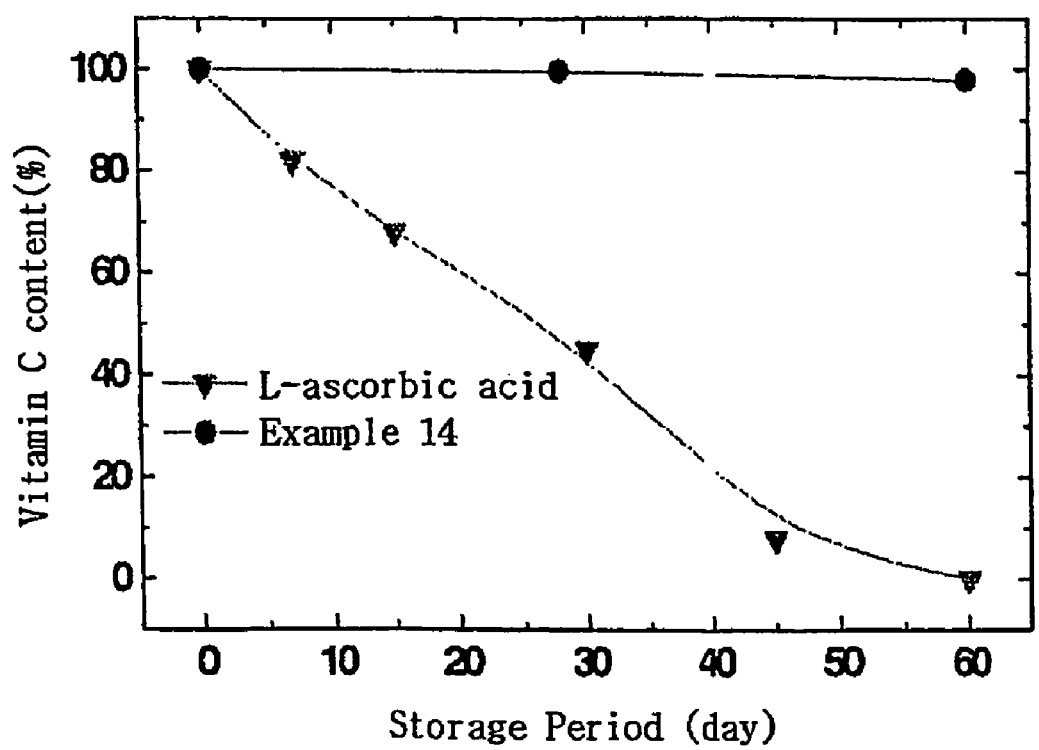
FIG. 24 is a graph showing the storage stability evaluation results of vitamin C hybrid materials prepared in Example 12.

Storage stability in an aqueous solution was evaluated for the hydrozincyte-type vitamin C hybrid material coated with silica, obtained in Example 12. From the analysis of the vitamin C hybrid material powder obtained in Example 12, the content of vitamin C was 25 wt %. 400 mg of the powder was added to 10 mL of decarboxylated distilled water, and sealed. Then, while storing the hybrid material in a constant-temperature oven at 42° C., the content of vitamin C was periodically examined using HPLC. In order to compare stability, 100 mg of pure vitamin C (L-ascorbic acid) was stored in the same condition, and a change of the vitamin content was examined. FIG. 24 is a graph showing the changes of the vitamin C contents depending on the storage period. This shows that the vitamin C content of the hybrid material according to the present invention did not show significant change, while vitamin C was destroyed very rapidly in the pure vitamin C.

Example 24

Figure 25:
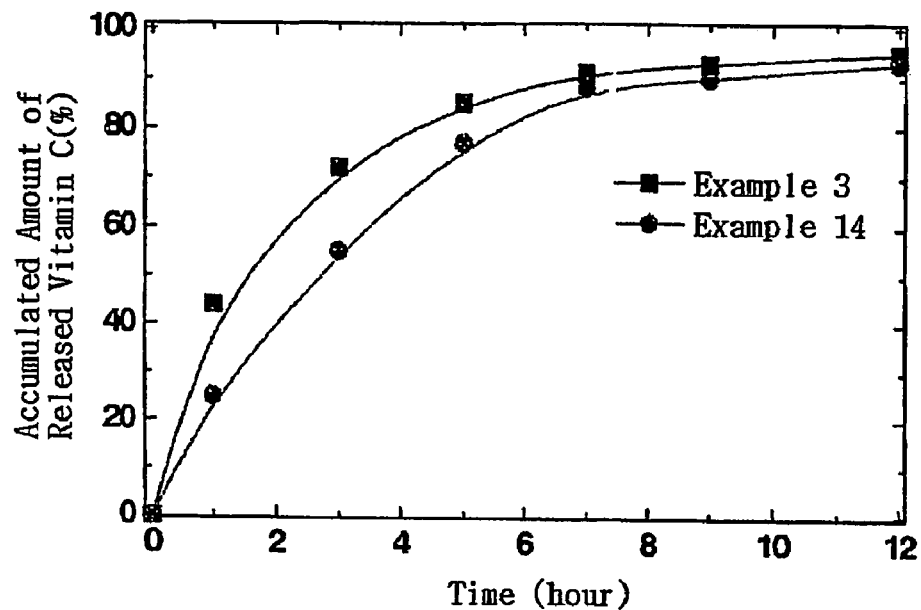
FIG. 25 is a graph showing the time-dependent elution pattern of vitamin C hybrid materials prepared in Examples 3 and 12.

Sustained-release property was evaluated for the vitamin C hybrid material obtained in Examples 3 and 12. For this, 0.00738 mol of the hybrid material powder was added to 25 ml of 0.8% NaCl aqueous solution, and with stirring uniformly at 37° C., the released amount of vitamin C depending on time was measured through an absorption intensity at 265 nm of ultraviolet absorption spectrum. The results are shown in FIG. 25. As seen from FIG. 25, in the present experimental condition, vitamin C was released continuously as time lapsed, which shows that the vitamin hybrid material according to the present invention has a good sustained-release property.

Example 25

Figure 26:
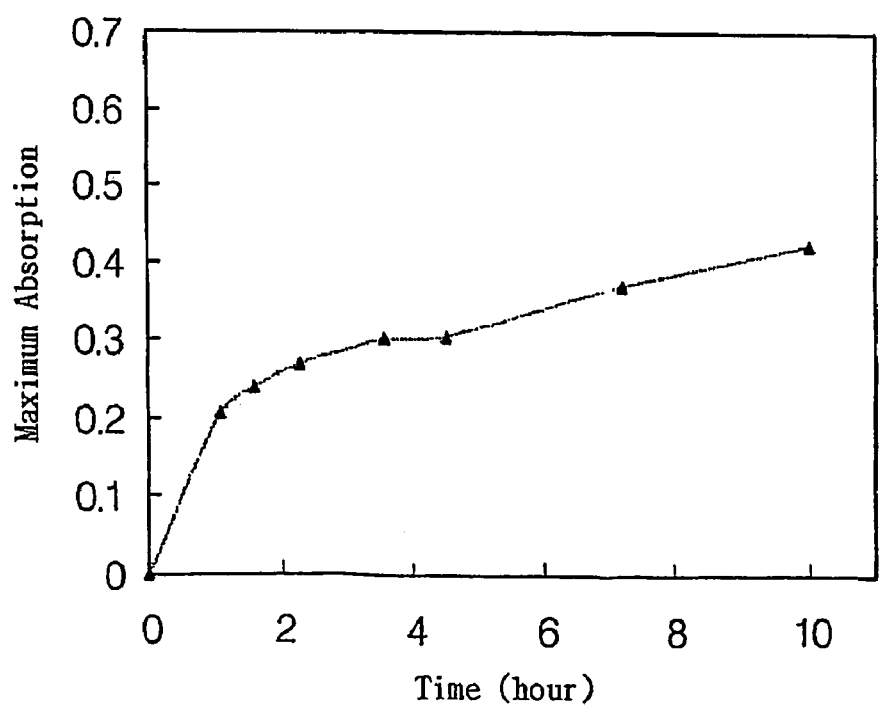
FIG. 26 is a graph showing the time-dependent elution pattern of indol-3-acetic acid in 0.8% NaCl aqueous solution for $Zn_5(OH)_8(C_{10}H_8NO_2)_2 \cdot nH_2O$ hybrid materials prepared by the coprecipitation method.

A sustained-release property of indol-3-acetic acid molecules was evaluated for the indol-3-acetic acid hybrid material obtained in Example 11. For this, 0.5 g of the hybrid material was added to 25 ml of 0.8% NaCl aqueous solution, and with stirring uniformly at 37° C., the released amount of vitamin C depending on time was measured through high performance liquid chromatography (HPLC). FIG. 26 is a graph showing a release rate of indol-3-acetic acid measured in this way, which shows that indol-3-acetic acid anions stabilized between the layers were slowly released by the ion-exchange with $Cl^-$ ions in the saline solution.

While the present invention has been particularly shown and described with reference to exemplary embodiments thereof, it will be understood by those of ordinary skill in the art that various changes in form and details may be made therein without departing from the spirit and scope of the present invention as defined by the following claims.

The invention claimed is:

1. A hybrid material in particle form comprising an active component for cosmetics and a layered metal hydroxide, wherein said active component includes at least one selected from the group consisting of vitamin C, tocopherol succinate, tocopheryl acetate, citric acid, and indol-3-acetic acid, wherein said active component is present in its anionic form between layers of said layered metal hydroxide and wherein said hybrid material is for the use in cosmetics.

2. The hybrid material according to claim 1, wherein said active component includes vitamin C.

3. The hybrid material according to claim 1, wherein said layered metal hydroxide is a hydroxy double salt.

4. The hybrid material according to claim 1, wherein said layered metal hydroxide is a layered double hydroxide.

5. The hybrid material according to claim 1, wherein a surface of the hybrid material is coated.

6. The hybrid material according to claim 5, wherein the surface is coated with silica.

7. The hybrid material according to claim 5, wherein the surface is coated with at least one coating material selected from the group consisting of polyvinyl alcohol, polyethylene glycol, cellulose, polymethyl methacrylate and silane.

8. A method for preparing the hybrid material according to claim 1, comprising dissolving at least one said active component and at least one starting material for said layered metal hydroxide in an aqueous solvent or a mixed solvent to precipitate said hybrid material.

9. The method according to claim 8, wherein said active component includes at least one selected from the group consisting of vitamin C, tocopherol succinate, tocopheryl acetate, citric acid, and indol-3-acetic acid.

10. A method for preparing the hybrid material according to claim 1, the method comprising:
    forming a metal hydroxide salt from at least one starting material for said layered metal hydroxide in a basic solution;
    dispersing said layered metal hydroxide salt in an aqueous solvent or a mixed solvent; and
    dissolving said active component to cause an ion-exchange reaction.

11. The method according to claim 8, further comprising applying a coating onto a surface of the hybrid material.

12. The method according to claim 11, wherein said coating is a silica coating.

13. The method according to claim 11, wherein said coating is applied with at least one coating material selected from the group consisting of polyvinyl alcohol, polyethylene glycol, cellulose, polymethyl methacrylate and silane.

14. A cosmetic composition comprising the hybrid material according to claim 1.

15. The hybrid material according to claim 1, wherein said active component is stabilized in said hybrid material sufficiently for the use in cosmetics.

16. The hybrid material according to claim 1, wherein said active component is indole-3-acetic acid.

17. The hybrid material according to claim 1, wherein said active component is tocopherol succinate.

18. The hybrid material according to claim 1, wherein a metal in said layered metal hydroxide is at least one selected from the group consisting of Zn(II), Mg(II), Ca(II), and Al(III).

19. The hybrid material according to claim 18, wherein said layered metal hydroxide is a hydroxyl double salt.

20. The hybrid material according to claim 19, wherein a metal in said hydroxyl double salt is Zn(II).

21. The method according to claim 8, wherein said vitamin C is either L-ascorbic acid or ascorbate.

22. The method according to claim 8, wherein said starting material is selected from at least one selected from the group consisting of a metal carbonate, a metal chloride, a metal nitrate and an organic metal salt.

23. The method according to claim 22, wherein said organic metal salt is selected from the group consisting of a metal acetate, metal oxalate and metal citrate.

24. The method according to claim 8, wherein a metal in said layered metal hydroxide is at least one selected from the group consisting of Zn(II), Mg(II), Ca(II), and Al(III).

25. The method according to claim 8, wherein said starting material is at least one selected from the group consisting of $ZnCl_2$, $MgCl_2$, $AlCl_3$, $Zn(CH_3COO)_2$, $CaCl_2$, and $Zn(NO_3)_2$.

26. A method for stabilizing an active component in a cosmetic composition, comprising incorporating said active component in its anionic form between layers of a layered metal hydroxide to form a hybrid material in particle form comprising said active component in a stabilized form, wherein said active component includes at least one selected from the group consisting of vitamin C, tocopherol succinate, tocopheryl acetate, citric acid and indol-3-acetic acid.

27. The method according to claim 26, wherein said active component is vitamin C.

28. The method according to claim 26, wherein a metal in said layered metal hydroxide is at least one selected from the group consisting of Zn(II), Mg(II), Ca(II), and Al(III).

29. The method according to claim 28, wherein said metal is Zn(II).

30. The method according to claim 28, wherein said layered metal hydroxide is a hydroxy double salt or a layered double hydroxide.

31. The method according to claim 30, wherein said layered metal hydroxide is a hydroxyl double salt containing Zn(II).

32. The hybrid material prepared by the method of claim 8.

33. A method for preparing a hybrid material comprising an active component for cosmetics and a layered metal hydroxide, which comprises
reacting at least one starting material for said layered metal hydroxide with an organic acid or an anionic surfactant in an aqueous solvent or a mixed solvent to form a coprecipitate of an organic-inorganic layered hybrid material;
dispersing said organic-inorganic layered hybrid material in an aqueous solvent or a mixed solvent; and
adsorbing said active component onto said organic-inorganic layered hybrid material, wherein said active component is selected from the group consisting of retinol, retinal acetate, retinyl palmitate, α-tocopherol and tocopheryl acetate.

34. The hybrid material prepared by the method of claim 33.

35. A cosmetic composition comprising the hybrid material according to claim 32.

36. The hybrid material according to claim 1, wherein said active component includes citric acid.

37. The method according to claim 33, wherein said organic acid is selected from the group consisting of citric acid, stearic acid, succinic acid, tocopherol succinate and tocopheryl acetate, to form a coprecipitate.

38. The method according to claim 33, wherein said anionic surfactant is dodecyl sulfate.

* * * * *